United States Patent [19]

Mafoti

[11] Patent Number: 5,109,034

[45] Date of Patent: Apr. 28, 1992

[54] STORAGE STABLE SOLID ISOCYANATE COMPOSITIONS, PREPARATION, AND METHOD OF USE THEREOF

[75] Inventor: Robson Mafoti, Pittsburgh, Pa.

[73] Assignee: Miles Inc., Pittsburgh, Pa.

[21] Appl. No.: 709,530

[22] Filed: Jun. 3, 1991

Related U.S. Application Data

[62] Division of Ser. No. 454,215, Dec. 21, 1989, Pat. No. 5,043,472.

[51] Int. Cl.⁵ .............................................. C08G 18/14
[52] U.S. Cl. ..................................... 521/159; 528/59; 528/60; 528/61; 528/62; 528/63; 528/64; 528/65; 528/66
[58] Field of Search ................ 528/59, 60, 61, 62, 528/63, 64, 65, 66; 521/159

[56] References Cited

U.S. PATENT DOCUMENTS

| | | | |
|---|---|---|---|
| 3,152,162 | 10/1964 | Fischer et al. | 260/453 |
| 3,384,653 | 5/1968 | Erner et al. | 260/453 |
| 3,394,164 | 7/1968 | McClellan et al. | 260/453 |
| 3,394,165 | 7/1968 | McClellan et al. | 260/453 |
| 3,449,256 | 6/1969 | Farrissey et al. | 252/182 |
| 3,457,200 | 7/1969 | Critchfield et al. | 260/2.5 |
| 3,585,230 | 6/1971 | Woycheshin et al. | 260/153 |
| 3,640,966 | 2/1972 | Hennig et al. | 260/77.5 R |
| 3,641,093 | 2/1972 | Brooks et al. | 260/453 AR |
| 3,644,457 | 2/1972 | König | 560/351 |
| 3,674,828 | 7/1972 | Brooks et al. | 260/453 P |
| 3,701,796 | 10/1972 | Saaty et al. | 260/453 SP |
| 3,883,571 | 5/1975 | Allport et al. | 260/453 AM |
| 3,892,691 | 7/1975 | White et al. | 260/2.5 AM |
| 4,014,935 | 3/1977 | Ibbotson | 260/566 R |
| 4,031,026 | 6/1977 | Ibbotson | 252/182 |
| 4,055,548 | 10/1977 | Carleton et al. | 260/77.5 AT |
| 4,072,712 | 2/1978 | Meisert et al. | 260/566 R |
| 4,088,665 | 5/1978 | Findeisen et al. | 260/453 AM |
| 4,102,833 | 7/1978 | Salisbury | 521/159 |
| 4,115,428 | 9/1978 | Vidal et al. | 260/449 L |
| 4,118,411 | 10/1978 | Reiff et al. | 260/453 SP |
| 4,143,063 | 3/1979 | Alberino et al. | 260/453 SP |
| 4,154,752 | 5/1979 | Sundermann et al. | 260/453 SP |
| 4,177,205 | 12/1979 | Schaaf et al. | 260/453 AM |
| 4,229,347 | 10/1980 | Holt et al. | 260/239 A |
| 4,332,742 | 6/1982 | Allen | 260/453 SP |

*Primary Examiner*—Maurice J. Welsh
*Attorney, Agent, or Firm*—Joseph C. Gil; Richard E. L. Henderson

[57] ABSTRACT

This invention relates to a storage-stable solid isocyanate compositions that are substantially crystalline at room temperature comprising the reaction products of organic isocyanates with substoichiometric quantities of 2-methyl-1,3-propanediol.

This invention further to a method of using the solid isocyanate compositions of the invention in the preparation of polyurethane products.

2 Claims, No Drawings

STORAGE STABLE SOLID ISOCYANATE COMPOSITIONS, PREPARATION, AND METHOD OF USE THEREOF

This application is a division of application Ser. No. 07/454,215 filed Dec. 21, 1989, now U.S. Pat. No. 5,043,472.

BACKGROUND OF THE INVENTION

This invention relates to storage-stable solid isocyanate compositions that are substantially crystalline at room temperature comprising reaction products of organic isocyanates and substoichiometric quantities of 2-methyl-1,3-propanediol.

It has generally been asserted that diisocyanates that are liquid at room temperature (i.e., approximately 25° C.) have advantages over solid diisocyanates, at least in part because liquid isocyanates are said to be easier to handle and mix than are solid diisocyanates. In particular, the known solid diisocyanates melt so nearly at room temperature that handling is cumbersome or melt at such high temperatures that they are unsuitable for the normally used reaction techniques. As a result, much effort has been made to convert solid diisocyanates to liquid derivatives and to convert liquid diisocyanates to more easily and safely handled liquid derivatives.

The most important commercially available diisocyanates that are solid at room temperature are diphenylmethane-4,4'-diisocyanate and its 2,4'-isomer, which melt at 39° C. and 34.5° C., respectively. Numerous patent references relating to the preparation of liquid diphenylmethane diisocyanates have issued. Some of these approaches include the reaction of the diisocyanate with N,N-di(2-hydroxypropyl)aniline in the presence of phosphoric acid (U.S. Pat. No. 3,394,165); the introduction of carbodiimide groups into the isocyanate (U.S. Pat. Nos. 4,177,205, 4,154,752. 4,143,063, 4,088,665, 4,072,712, 4,014,935, 3,641,093, 3,640,966, and 3,152,162); the reaction of the isocyanate with (i) polyoxyethylene glycols (U.S. Pat. Nos. 4,115,428 and 4,055,548), (ii) propylene and other alkylene glycols (U.S. Pat. Nos. 4,229,347, 4,118,411, 3,892,691, and 3,883,571), (iii) N,N'-disubstituted thioureas (U.S. Pat. No. 3,674,828), (iv) N-substituted ethanolamine (U.S. Pat. No. 4,332,742), and (v) low molecular weight polyether polyols (U.S. Pat. No. 4,102,833); the addition of an organosilicone (U.S. Pat. No. 3,585,230); the addition of a dibenzoate (U.S. Pat. No. 3,701,796); and the combination of partial carbodiimidization with a reaction product of the isocyanate and a diol (U.S. Pat. No. 4,031,026).

Other methods have been used to liquefy diphenylmethane-4,4'-diisocyanate, as well as mixtures of the diphenylmethane-4,4'-diisocyanate with small amounts of the 2,4'-isomer. For example, U.S. Pat. No. 3,644,457 discloses the reaction of diphenylmethane diisocyanate with substoichiometric quantities of certain branched aliphatic diols, such as 1,3-propanediols having at least two alkyl substituents or poly-1,2-propylene ether glycols. Because only 0.1-0.3 molar quantities of the diols are used, the resultant liquid product consists of unreacted diphenylmethane diisocyanate and various adducts of the diols with the isocyanate. The freezing point depression of the isocyanate caused by the presence of the adducts, and thus the viscosity of the resultant product, can be varied by adjusting the number of adducts. In the absence of alkyl substitution, however, aliphatic diols form solids or gels when reacted with excess diphenylmethane diisocyanate. While liquified products made according to this patent have met with commercial success, they still suffer from a serious drawback. Specifically, these products solidify at temperatures near room temperature. As a result, these materials must be kept warm during transport and storage or else must be melted before use, particularly in cold climates. At the same time, the products are too easily melted to be stored as solids, particularly in warm climates.

Other attempts to form liquid diphenylmethane diisocyanates have been described, for example, in U.S. Pat. Nos. 3,449,256, 3,394,164, and 3,384,653, and are based on the addition of a trihydrocarbyl phosphate or small amounts of phosphoric acid. The storage stability of products prepared according to these patents is quite good around room temperature, but as the temperature decreases, such materials tend to solidify.

Conventionally used diisocyanates that are liquid at room temperature, such as toluene diisocyanate or hexamethylene diisocyanate, are generally physiologically harmful because of their high vapor pressure. As a result, such diisocyanates can be used only if certain safety precautions are observed. Consequently, various attempts have been made to apply certain techniques to reduce the physiological effects of isocyanates that are liquid at room temperature. Such techniques, however, usually produce diisocyanates having higher molecular weight or isocyanates of higher valency (i.e., tri- or polyisocyanates) or isocyanates having a combination of such properties.

U.S. Pat. No. 3,457,200 discloses the use of reaction products of toluene diisocyanate with certain low molecular weight diols in the preparation of flexible polyurethane foams. Suitable diols included certain branched aliphatic diols, some of which are similar to diols described in U.S. Pat. No. 3,644,457 for use with diphenylmethane diisocyanates. Not all such diols were found suitable, however, because the resultant products were solids having melting points significantly above room temperature. Moreover, because of reactions between the isocyanate and the urethane hydrogens, even the useful reaction products were said not to be sufficiently storage stable. As a result, the diisocyanate-diol reaction products must be stabilized by reaction with benzoyl chloride or other stabilizing agents.

It is thus apparent that the search for commercially acceptable liquid diphenylmethyl diisocyanates is continuing. Nevertheless, solid diisocyanates having appropriate physical and chemical properties would have certain advantages. For example, a solid diisocyanate that would melt at a temperature in the range normally used to prepare polyurethanes products, for example, about 95°-160° C., could be added to a foamable mixture where it would melt in situ or could be preheated to the reaction temperature before being added to the foamable mixture. It would be particularly advantageous to use a sharply melting crystalline solid diisocyanate that could be ground into a fine crystal or powder for ease in handling and mixing.

It was, therefore, an object of this invention to obtain improved storage-stable organic diisocyanate compositions that are solid even at temperatures higher than room temperature. It has now surprisingly been found that the reaction of certain diisocyanates and higher order isocyanates with 2-methyl-1,3-propanediol produces storage-stable isocyanate compositions that are sharply melting, substantially crystalline solids at room temperature and can be ground into fine crystals or powders. The compositions of the invention have been found eminently suitable for the preparation of polyurethane foams, elastomers, and other polyurethane products.

SUMMARY OF THE INVENTION

This invention relates to storage-stable solid isocyanate compositions, wherein said isocyanate compositions are substantially crystalline at room temperature, comprising the reaction product of an organic isocyanate and substoichiometric quantities of 2-methyl-1,3-propanediol, wherein from 1.2 to 6 moles of said organic isocyanate is used for each mole of 2-methyl-1,3-propanediol.

This invention further relates to a method of using the isocyanate compositions of the invention in the preparation of polyurethane products.

DETAILED DESCRIPTION OF THE INVENTION

The present invention relates to novel storage stable isocyanate compositions which are substantially crystalline at or above room temperature. The isocyanate compositions of the invention comprise the reaction products of various organic diisocyanates and higher order isocyanates with substoichiometric quantities of 2-methyl-1,3-propanediol and have isocyanate contents of from about 6 to about 26% by weight.

Although 2-methyl-1,3-propanediol is an assymmetrical compound and might be expected to give rise to relatively low-melting products, the isocyanate compositions of the invention, surprisingly, are substantially crystalline solids having sharp melting points or narrow melting ranges. In addition to physical appearance, crystallinity can be established by differential scanning calorimetry ("DSC") and wide-angle X-ray diffraction studies. The isocyanate compositions, advantageously, are solids at temperatures above the melting points of the starting isocyanates, some of which are liquids at or near room temperature. In addition, because of the very narrow melting ranges, the isocyanate compositions of the invention do not become soft or sticky at temperatures below their melting points but remain solid until melting begins.

The solid isocyanate compositions of the invention can be ground or milled into fine crystals or powders for easier handling and mixing. The fine crystals and powder forms are, surprisingly, also storage stable.

Suitable isocyanates used in the preparation of the compositions of the invention include aliphatic, cycloaliphatic, araliphatic, aromatic and heterocyclic polyisocyanates of the type described, for example, by W. Siefken in *Justus Liebigs Annalen der Chemie*, 562, pages 75 to 136. Examples of suitable diisocyanates include ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and -1,4-diisocyanate, and mixtures of these isomers; 1-isocyanato-3,3,5-trimethyl-5-isocyanatomethylcyclohexane (see, e.g. German Auslegeschrift 1,202,785 and U.S. Pat. No. 3,401,190); 2,4- and 2,6-hexahydrotoluene diisocyanate and mixtures of these isomers; hexahydro-1,3- and/or -1,4-phenylene diisocyanate; perhydro-2,4'- and/or -4,4'-diphenylmethane diisocyanate ("HMDI"); 1,3- and 1,4-phenylene diisocyanate; 2,4- and 2,6-toluene diisocyanate and mixtures of these isomers ("TDI"); diphenylmethane-2,4'- and/or -4,4'-diisocyanate ("MDI"); and naphthylene-1,5-diisocyanate. Examples of higher order isocyanates include triphenylmethane-4,4',4''-triisocyanate; polyphenyl-polymethylene-polyisocyanates of the type which may be obtained by condensing aniline with formaldehyde, followed by phosgenation (also known as crude, or polymeric, MDI), which are described, for example, in British Patents 878,430 and 848,671; m- and p-isocyanatophenyl sulfonyl isocyanates of the type described in U.S. Pat. No. 3,454,606; perchlorinated aryl polyisocyanates of the type described, for example, in U.S. Pat. No. 3,227,138; modified polyisocyanates containing carbodiimide groups of the type described in U.S. Pat. No. 3,152,162; diisocyanates of the type described in U.S. Pat. No. 3,492,330; modified polyisocyanates containing allophanate groups of the type described, for example, in British Patent 994,890, Belgian Patent 761,616, and published Dutch Patent Application 7,102,524; modified polyisocyanates containing isocyanurate groups of the type described, for example, in U.S. Pat. No. 3,002,973, in German Patentschriften 1,022,789, 1,222,067 and 1,027,394, and in German Offenlegungsschriften 1,919,034 and 2,004,048; modified polyisocyanates containing urea groups of the type described in German Patentschrift 1,230,778; polyisocyanates containing biuret groups of the type described, for example, in German Patentschrift 1,101,394, U.S. Pat. Nos. 3,124,605 and 3,201,372, and in British Patent 889,050; polyisocyanates obtained by telomerization reactions of the type described, for example, in U.S. Pat. No. 3,654,106; polyisocyanates containing ester groups of the type described, for example, in British Patents 965,474 and 1,072,956, in U.S. Pat. No. 3,567,763, and in German Patentschrift 1,231.688; reaction products of the above-mentioned isocyanates with acetals as described in German Patentschrift 1,072,385; and polyisocyanates containing polymeric fatty acid groups of the type described in U.S. Pat. No. 3,455,883. It is also possible, but less preferred, to use the isocyanate-containing distillation residues accumulating in the production of isocyanates on a commercial scale. Certain mixtures of the aforementioned polyisocyanates may also be suitable.

It is particularly preferred to use readily available diisocyanates, such as diphenylmethane-2,4'- and/or -4,4'-diisocyanate and mixtures of the isomers ("MDI"); 2,4- and 2,6-toluene diisocyanates and mixtures of the isomers ("TDI"); perhydro-2,4'- and/or -4,4'-diphenylmethane diisocyanate, also known as dicyclohexylmethane-2,4'- and/or -4,4'-diisocyanate. Particularly preferred is MDI, most preferably the 4,4'-isomer. Polyphenyl-polymethylene-polyisocyanates (crude, or polymeric, MDI), are suitable but less preferred.

In the preparation of the isocyanate compositions of the invention, the starting isocyanate reacts with substoichiometric quantities of 2-methyl-1,3-propanediol in a molar ratio of about 1.2 to about 6, wherein the isocyanate content of the resultant compositions is, for example, about 6 to about 26 percent by weight, depending on the particular starting isocyanate used in the reaction. For example, when the preferred diphenylmethyl diisocyante is used, the preferred isocyanate content ranges from about 9 to about 26 percent by weight of the resultant isocyanate composition. When toluene diisocyanate, hydrogenated MDI, or polymeric MDI are used, the preferred isocyanate content ranges from about 6 to about 15 percent by weight of the resultant isocyanate composition. Compositions based on TDI, HMDI, and polymeric MDI having an isocyanate content above about 15 percent by weight are pasty rather than solid. One skilled in the art can, however, readily determine the appropriate molar ratio of isocyanate to 2-methyl-1,3-propanediol that produces suitable compositions.

The reaction of the organic isocyanate and 2-methyl-1,3-propanediol can be carried out at temperatures ranging from room temperature (i.e., about 25° C.) up to about 125° C. The preferred reaction temperature is in the range of 25° C. to about 90° C., most preferably from about 40° C. to about 80° C. Because the reaction can generally be carried out at relatively low temperatures, the isocyanate structure of the isocyanate compositions of the invention is essentially completely preserved. For example, allophanate formation by the reaction of urethane groups with isocyanate groups apparently does not take place to any large extent, even when the reaction product is formed at a temperature as high as 125° C.

The process for preparing the compositions of the invention may be carried out by introducing 2-methyl-1,3-propanediol into the organic isocyanate at temperatures of from room temperature up to about 125° C. with stirring. When the starting isocyanate is solid at room temperature, such as when MDI is used, the isocyanate is preferably melted before the diol is added. Alternatively, the isocyanate can be introduced into the diol. The isocyanate compositions of the invention solidify as the reaction goes to completion or upon cooling.

The isocyanate compositions of the invention can be used for all types of polyaddition reactions in the lacquer and plastics industries, for example, for the production of polyurethane foams or polyurethane elastomers, using techniques and materials generally known and used in the art. The isocyanate compositions can be used as the sole isocyanate component in the manufacture of polyurethane or they may be blended with other isocyanates. Because they are solids, the materials can be easily transported and stored at temperatures normally encountered during transport or storage.

Suitable hydroxyl-containing compounds for use in preparing polyurethane products using the compositions of this invention are those conventionally used in polyurethane chemistry, including as hydroxyl-containing polyethers, polyesters, polyacetals, polycarbonates, polyesterethers, polythioethers, polyamides, polyesteramides, polysiloxanes, polybutadienes, and polyacetones, and can optionally contain one or more isocyanate-reactive amino groups. Suitable hydroxyl-containing compounds have average molecular weights in the range of about 400 to about 10,000 (preferably about 750 to about 6000) and contain 2 to 4 reactive hydroxyl groups or, less preferably, 1 to 3 reactive hydroxyl groups and 1 to 3 reactive primary or secondary amino groups. Particularly preferred hydroxyl-group-containing compounds include polyethers or polyesters having 2 to 3, preferably 2, isocyanate-reactive hydroxyl groups.

Suitable hydroxyl-containing polyethers are known and may be prepared, for example, by the polymerization of epoxides such as ethylene oxide, propylene oxide, butylene oxide, tetrahydrofuran, styrene oxide, or epichlorohydrin, optionally in the presence of $BF_3$, or by chemical addition of such epoxides. optionally as mixtures or successively, to starting components containing reactive hydrogen atoms, such as water, alcohols, or amines. Examples of such starting components include ethylene glycol, 1,3- or 1,2-propanediol. 1,2-, 1,3-, or 1,4-butanediol, trimethylolpropane, 4,4'-dihydroxydiphenylpropane, aniline, ammonia, ethanolamine, or ethylene diamine. Sucrose polyethers of the type described, for example, in German Auslegeschriften 1,176,358 and 1,064,938 may also be used according to the invention. Polyethers which contain predominantly primary hydroxyl groups (up to about 90% by weight, based on all of the hydroxyl groups in the polyether) are also often preferred. Polyethers modified by vinyl polymers of the kind obtained, for example, by the polymerization of styrene and acrylonitrile in the presence of polyethers (e.g., U.S. Pat. Nos. 3,383,351, 3,304,273, 3,523,093, and 3,110,695 and German Patentschrift 1,152,536) are also suitable, as are polybutadienes containing hydroxyl groups. Particularly preferred polyethers include polyoxyalkylene polyether polyols, such as polyoxyethylene diol, polyoxypropylene diol, polyoxybutylene diol, and polytetramethylene diol.

Suitable hydroxyl-containing polyesters include reaction products of polyhydric alcohols (preferably diols), optionally with the addition of trihydric alcohols, and polybasic (preferably dibasic) carboxylic acids. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic, or heterocyclic and may be substituted, e.g. by halogen atoms, and/or unsaturated. Suitable polycarboxylic acids include succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, dimethyl terephthalic, and terephthalic acid bis-glycol esters. Suitable polyhydric alcohols include ethylene glycol, 1,2- and 1,3-propanediol, 1,4- and 2,3-butane diol, 1,6-hexanediol, 1,8-octanediol, neopentyl glycol, cyclohexanedimethanol, 1,4-bis(hydroxymethyl)cyclohexane, 2-methyl-1,3-propanediol, glycerol, trimethylolpropane, 1,2,6-hexanetriol, 1,2,4-butanetriol, trimethylolethane, pentaerythritol, quinitol, mannitol, sorbitol, methyl glycoside, diethylene glycol, triethylene glycol, tetraethylene glycol, polyethylene glycols, dipropylene glycol, polypropylene glycols, dibutylene glycol, and polybutylene glycols. The polyesters may also contain a proportion of carboxyl end groups. Polyesters of lactones, such as ε-caprolactone, or of hydroxycarboxylic acids, such as ω-hydroxycaproic acid, may also be used. Hydrolytically stable polyesters are preferably used in order to obtain the greatest benefit relative to the hydrolytic stability of the final product. Preferred polyesters include polyesters obtained from adipic acid or isophthalic acid and straight chained or branched diols, as well as lactone polyesters, preferably those based on caprolactone and diols.

Suitable polyacetals include compounds obtained from the condensation of glycols, such as diethylene glycol, triethylene glycol, 4,4'-dihydroxydiphenylmethane, and hexanediol, with formaldehyde or by the polymerization of cyclic acetals, such as trioxane.

Suitable polycarbonates include those prepared by the reaction of diols, such as 1,3-propanediol, 1,4-butanediol, 1,6-hexanediol, diethylene glycol, triethylene glycol, tetraethylene glycol, or thiodiglycol, with phosgene or diarylcarbonates such as diphenylcarbonate (German Auslegeschriften 1,694,080, 1,915,908, and 2,221,751; German Offenlegungsschrift 2,605,024).

Suitable polythioethers include the condensation products obtained by the reaction of thiodiglycol, either alone or with other glycols, dicarboxylic acids, formaldehyde, aminocarboxylic acids, or amino alcohols. The products obtained are polythio-mixed ethers, polythioether esters, or polythioether ester amides, depending on the components used.

Suitable polyester amides and polyamides include, for example, the predominantly linear condensates prepared from polybasic saturated and unsaturated carboxylic acids or the anhydrides thereof and polyvalent saturated or unsaturated amino alcohols, diamines, polyamines, and mixtures thereof.

Other suitable hydroxyl-containing compounds include polyhydroxyl compounds already containing urethane or urea groups and modified or unmodified natural polyols. Products of addition of alkylene oxides to phenol-formaldehyde resins or to urea-formaldehyde resins are also suitable. Furthermore, amide groups may be introduced into the polyhydroxyl compounds as described, for example, in German Offenlegungsschrift 2,559,372.

Polyhydroxyl compounds in which polyadducts or polycondensates or polymers are present in a finely dispersed or dissolved form may also be used according to the invention, provided that the molecular weights range from about 750 to about 3500. Polyhydroxyl compounds of this type may be obtained, for example, by carrying out polyaddition reactions (e.g., reactions between polyisocyanates and amino functional compounds) or polycondensation reactions (e.g., between formaldehyde and phenols or amines) in situ in the above-mentioned hydroxyl-containing compounds. Processes of this type are described, for example, in German Auslegeschriften 1,168,075 and 1,260,142 and German Offenlegungsschriften 2,324,134, 2,423,984, 2,512,385, 2,513,815, 2,550,796, 2,550,797, 2,550,833, 2,550,862, 2,633,293, and 2,639,254. Suitable compounds may also be obtained according to U.S. Pat. Nos. 3,869,413 or 2,550,860 by mixing a previously prepared aqueous polymer dispersion with a polyhydroxyl compound and then removing water from the mixture.

Polyhydroxyl compounds modified with vinyl polymers, such as those obtained, for example, by the polymerization of styrene and acrylonitrile in the presence of polycarbonate polyols (German Patentschrift 1,769,795 and U.S. Pat. No. 3,637,909) are also suitable for the preparing prepolymers suitable for the process of the invention. Synthetic resins with exceptional flame resistance may be obtained by using polyether polyols which have been modified by graft polymerization with vinyl phosphonic acid esters and optionally (meth)acrylonitrile, (meth)acrylamide, or hydroxyfunctionalized (meth)acrylic acid esters according to German Offenlegungsschriften 2,442,101, 2,644,922, and 2,646,141.

Suitable, although less preferred, hydroxyl-containing compounds include organofunctional polysiloxanes containing two terminal isocyanate-reactive groups and structural units of the formula —O—Si(R)$_3$ in which R denotes a $C_1$–$C_4$ alkyl group or a phenyl group, preferably a methyl group. Both the known, pure polysiloxanes containing organofunctional end groups and the known siloxane polyoxyalkylene copolymers containing organofunctional end groups are suitable starting materials according to the invention.

Also suitable are so-called amine terminated polyethers containing primary or secondary (preferably primary) aromatically or aliphatically (preferably aliphatically) bound amino groups. Compounds containing amino end groups can also be attached to the polyether chain through urethane or ester groups. These amine terminated polyethers can be prepared by any of several methods known in the art. For example, amine terminated polyethers can be prepared from polyhydroxyl polyethers (e.g., polypropylene glycol ethers) by a reaction with ammonia in the presence of Raney nickel and hydrogen (Belgian Patent 634,741). Polyoxyalkylene polyamines can be prepared by a reaction of the corresponding polyol with ammonia and hydrogen in the presence of a nickel, copper, chromium catalyst (U.S. Pat. No. 3,654,370). The preparation of polyethers containing amino end groups by the hydrogenation of cyanoethylated polyoxypropylene ethers is described in German Patentschrift 1,193,671. Other methods for the preparation of polyoxyalkylene (polyether) amines are described in U.S. Pat. Nos. 3,155,728 and 3,236,895 and in French Patent No. 1,551,605. French Patent No. 1,466,708 discloses the preparation of polyethers containing secondary amino end groups. Also useful are the polyether polyamines described in U.S. Pat. Nos. 4,396,729, 4,433,067, 4,444,910, and 4,530,941.

Relatively high molecular weight polyhydroxypolyethers suitable for the process of the present invention may be converted into the corresponding anthranilic acid esters by reaction with isatoic acid anhydride. Methods for making polyethers containing aromatic amino end groups are disclosed in German Offenlegungsschriften 2,019,432 and 2,619,840 and U.S. Pat. Nos. 3,808,250, 3,975,428, and 4,016,143. Relatively high molecular weight compounds containing amino end groups may also be obtained according to German Offenlegungsschrift 2,546,536 or U.S. Pat. No. 3,865,791 by reacting isocyanate prepolymers based on polyhydoxyl polyethers with hydroxyl-containing enamines, aldimines, or ketimines and hydrolyzing the reaction product.

Aminopolyethers obtained by the hydrolysis of compounds containing isocyanate end groups are preferred amine terminated polyethers. For example, in a process disclosed in German Offenlegungsschrift 2,948,419, polyethers containing hydroxyl groups (preferably two or three hydroxyl groups) react with polyisocyanates to form isocyanate prepolymers whose isocyanate groups are then hydrolyzed in a second step to amino groups. Preferred amine terminated polyethers are prepared by hydrolyzing an isocyanate compound having an isocyanate group content of from 0.5 to 40% by weight. The most preferred polyethers are prepared by first reacting a polyether containing two to four hydroxyl groups with an excess of an aromatic polyisocyanate to form an isocyanate terminated prepolymer and then converting the isocyanate groups to amino groups by hydrolysis. Processes for the production of useful amine terminated polyethers using isocyanate hydrolysis techniques are described in U.S. Pat. Nos. 4,386,218, 4,456,730, 4,472,568, 4,501,873, 4,515,923, 4,525,534, 4,540,720, 4,578,500, and 4,565,645; European Patent 097,299; and German Offenlegungsschrift 2,948,419, all the disclosures of which are herein incorporated by reference. Similar products are also described in U.S. Pat. Nos. 4,506,039, 4,525,590, 4,532,266, 4,532,317, 4,723,032, 4,724,252, and 4,855,504 and in U.S. application Ser. Nos. 07/232,302 (filed Aug. 17, 1988) and 07/389,384 (filed Aug. 2, 1989).

The amine terminated polyethers used in the present invention are in many cases mixtures with any of the above-mentioned compounds. These mixtures generally should contain (on a statistical average) two to three isocyanate reactive amino end groups.

General discussions of representative hydroxyl-containing compounds that may be used according to the present invention can be found, for example, in *Polyurethanes, Chemistry and Technology* by Saunders and Frisch, Interscience Publishers, New York, London, Volume I, 1962, pages 32-42 and pages 44-54, and Volume II, 1964, pages 5-6 and 198-199, and in *Kunststoff-Handbuch*, Volume VII, Vieweg-Höchtlen, Carl-Hanser-Verlag, Munich, 1966, on pages 45 to 71.

In preparing polyurethane products using the isocyanate compositions of this invention, it is also possible to use as chain-extending and crosslinking agents compounds having two or more isocyanate-reactive hydrogen atoms and having a molecular weight of from 32 to 399. Such compounds contain hydroxyl groups, amino groups, thiol groups, and/or carboxyl groups and generally contain 2 to 8 (preferably 2 to 4) isocyanate-reactive hydrogen atoms. Although hydroxyl-containing chain extenders and crosslinkers can be used, chain extenders and crosslinkers containing amino groups are preferred. The preferred amine chain extenders contain exclusively aromatically bound primary or secondary (preferably primary) amino groups and preferably also contain alkyl substituents. Examples of such diamines include 1,4-diaminobenzene, 2,4-diaminotoluene, 2,4'- and/or 4,4'-diaminodiphenylmethane, 3,3'-dimethyl-4,4'-diaminodiphenylmethane, 1-methyl-3,5-bis(methylthio)-2,4-and/or -2,6-diaminobenzene, 1,3,5-triethyl-2,4-diaminobenzene, 1,3,5-triisopropyl-2,4-diaminobenzene, 1-methyl-3,5-diethyl-2,4- and/or -2,6-diaminobenzene, 4,6-dimethyl-2-ethyl-1,3-diaminobenzene, 3,5,3',5'-tetraethyl-4,4-diaminodiphenylmethane, 3,5,3',5'-tetraisopropyl-4,4'-diaminodiphenylmethane, and 3,5-diethyl-3',5'-diisopropyl-4,4-diaminodiphenylmethane. Such diamines may, of course, also be used as mixtures. It is particularly preferred to use 1-methyl-3,5-diethyl-2,4-diaminobenzene or a mixture of this compound with 1-methyl-3,5-diethyl-2,6-diaminobenzene.

The less-preferred hydroxyl-containing chain extenders and crosslinkers include, in addition to the 2-methyl-1,3-propanediol used to prepare the solid isocyanate compositions of this invention, glycols and polyols, such as 1,2- and 1,3-propylene glycol, 1,4- and 2,3-butylene glycol, 1,6-hexanediol, 1,8-octanediol, neopentyl glycol, cyclohexanedimethanol, 1-methyl-1,3-propanediol, glycerol, trimethylolpropane, 1,2,6-hexanetriol, 1,2,4-butanetriol, and trimethylolethane.

In a one-shot process, for example, an isocyanate composition according to the invention can be mixed with the isocyanate-reactive components and other reactive or non-reactive ingredients. The resultant mixture can be heated until the isocyanate composition melts, at which point the reaction proceeds to form the polyurethane product.

The solid isocyanate composition may also be melted before addition to isocyanate-reactive components. Upon mixing with such isocyanate-reactive components, for example, in a closed mold using the well-known RIM method, the various reactive components react to form the polyurethane product.

Auxiliary agents and additives may, of course, optionally also be used in the preparation of polyurethane products using the isocyanate compositions of the invention. Suitable auxiliary agents and additives may include, for example, internal mold release agents, catalysts for the polyisocyanate-polyaddition reaction, blowing agents, surface-active additives, cell regulators, pigments, dyes, UV stabilizers, plasticizers, and fungistatic or bacteriostatic substances, such as those described in European Patent Application 81,701 at column 6, line 40, to column 9, line 31. When used, the preferred auxiliary agents and additives include known fillers and/or reinforcing substances, such as barium sulfate, kieselguhr, whiting, mica, and especially glass fibers, liquid crystal fibers, glass flakes, glass balls, aramide fibers, and carbon fibers.

One skilled in the art can readily envision other uses for the isocyanate composition of the invention.

The following examples further illustrate details for the preparation of the compounds of this invention. The invention, which is set forth in the foregoing disclosure, is not to be limited either in spirit or scope by these examples. Those skilled in the art will readily understand that known variations of the conditions and processes of the following preparative procedures can be used to prepare these compounds. Unless otherwise noted, all temperatures are degrees Celsius and all parts and percentages are parts and percentages by weight.

DESCRIPTION OF THE PREFERRED EMBODIMENTS

Examples 1 and 2

Examples 1 and 2 describe the preparation of products according to the invention based on diphenylmethane-4,4'-diisocyanate ("4,4'-MDI"). The use of different quantities of 2-methyl-1,3-propanediol produced compositions having different isocyanate contents.

Example 1

To 1925 parts by weight of a melt of 4,4'-MDI at 60° C. under a nitrogen atmosphere was added slowly with rapid stirring 175 parts by weight of 2-methyl-1,3-propanediol. The reaction was periodically cooled in an ice bath to prevent excessive heating. After one hour the viscous liquid was poured into a separate container where it immediately solidified. The resultant solid had an NCO content of 23 wt. % and melted sharply at about 107° C.

The product was analyzed by differential scanning calorimetry ("DSC"), which indicated major endotherms at 40° C. and 107° C. The lower temperature is attributable to melting of 4,4'-MDI and the higher temperature to melting of the reaction product. The presence of endotherms are indicative of crystalline products.

Wide-angle X-ray diffraction studies indicated a crystalline product.

The melting point and NCO content were monitored for about six weeks. No changes from the original values were observed.

Example 2

A product was prepared according to the method of Example 1 except that 1780 parts by weight of 4,4'-MDI and 320 parts by weight of 2-methyl-1,3-propanediol were used. The product solidified in the flask to give a product having an NCO content of 13.3 wt. % and a melting point of 148° C. The product was also stable upon storage.

DSC indicated major endotherms at 43° C. and 148° C., which are attributable to melting of 4,4'-MDI and the reaction product, respectively. The presence of endotherms are indicative of crystalline products.

Wide-angle X-ray diffraction studies indicated a crystalline product.

Examples 3 to 5

Examples 3-5 describe the preparation of products according to the invention based on toluene diisocyanate ("TDI"), dicyclohexylmethane-4,4'-diisocyanate (hydrogenated MDI, or "HMDI"), and a 2,4'-rich polymeric MDI.

Example 3

A product was prepared according to the method of Example 1 except that 1607 parts by weight of a mixture of 80 wt. % 2,4-TDI and 20 wt. % 2,6-TDI and 493 parts by weight of 2-methyl-1,3-propanediol were used. The product was obtained as a white crystalline solid having an NCO content of 14 wt. % and a melting range of 115°-120° C. The product was stable upon storage.

Example 4

A product was prepared according to the method of Example 1 except that 1764 parts by weight of dicyclohexylmethane 4,4'-diisocyanate and 336 parts by weight of 2-methyl-1,3-propanediol were used. Because the cycloaliphatic diisocyanate reacts more slowly than MDI, the reaction was performed at 85° C. The product was obtained as a white crystalline solid having an NCO content of 12 wt. % and a melting range of 110°-115° C. The product was stable upon storage.

Example 5

A product was prepared according to the method of Example 1 except for using a polymeric MDI having an isocyanate content of 32.9% and a functionality of 2.3. The polymeric MDI consisted of 78 wt. % monomeric diisocyanates (of which 22 wt. % is 2,4'-MDI and 32 wt. % is 2,2'-MDI, the rest being 4,4'-MDI), with the balance of the polymeric MDI being polyisocyanates having an isocyanate functionality greater than 2. The reaction used to prepare the product of the invention was performed at 70° C. using 1773 parts by weight of the polymeric MDI and 327 parts by weight of 2-methyl-1,3-propanediol. The product was obtained as a yellowish solid having an NCO content of 12.9 wt. % and a melting range of 105°-110° C. The product was stable upon storage.

Examples 6 to 8

Examples 6-8 are comparison examples for Example 1 in which products were prepared using diols other than 2-methyl-1,3-propanediol.

Example 6

A product was prepared according to the method of Example 1 except that 458 parts by weight of 4,4'-MDI and 42 parts by weight of 1,4-butanediol were used to prepare a product having an NCO content of 23 wt. %. The product was a white solid having a broad melting range of about 120°-185° C. and is, therefore, unsuitable for one-component urethane applications for which compositions of invention are useful.

Example 7

A product was prepared according to the method of Example 1 except that 469 parts by weight of 4,4'-MDI and 31 parts by weight of ethylene glycol were used to prepare a product having an NCO content of 23 wt. %. The product was a white solid having a broad melting range of about 50°-300° C. Even at 300° C. incompletely melted particles remained. The product was unsuitable for grinding into a powder.

Example 8

A product was prepared according to the method of Example 1 except that 462 parts by weight of 4,4'-MDI and 37 parts by weight of propylene glycol were used to prepare a product having an NCO content of 23 wt. %. The product was a white solid having a broad melting range of about 105°-160° C. The product was unsuitable for grinding into a powder using ordinary grinding techniques.

Example 9

The following procedure is used to prepare an elastomer according to the invention from a solid MDI-based isocyanate composition prepared according to Example 1. A blend was prepared using 187.5 parts by weight of a composition prepared according to Example 1, 312.5 parts by weight of a polytetramethylene glycol having a molecular weight of 2000, and 22.5 parts by weight of 1,4-butanediol. The mixture was degassed at about 60° C. for about two hours. The resultant bubble-free material was poured into a mold that was then placed into an oven at about 110° C. The temperature was maintained above the melting point of the MDI-based isocyanate composition (i.e., above about 107° C.) overnight. The resultant elastomer was removed from the mold and postcured at 100° C. for two hours. The properties of the elastomer are summarized in the following Table.

TABLE

| | |
|---|---|
| Shore A hardness | 90 |
| Tensile strength (N/mm$^2$) | 1092 |
| Tensile modulus (N/mm$^2$) | |
| At 100% | 5.3 |
| At 200% | 6.1 |
| Elongation (%) | 151 |
| Die C tear (N/mm) | 31.5 |
| Split tear (N/mm) | 5.3 |
| Compression set (%) | 51 |

What is claimed is:

1. A method of preparing a polyurethane comprising reacting
    (a) a storage-stable solid isocyanate composition that is substantially crystalline at room temperature, wherein said isocyanate composition comprises the reaction product of an organic isocyanate and 2-methyl-1,3-propanediol in quantities such that from 1.2 to 6 moles of said organic isocyanate are used for each mole of 2-methyl-1,3-propanediol, with
(b) an isocyanate-reactive compound.

2. A method of preparing a polyurethane comprising reacting
(a) a storage-stable solid isocyanate composition in the form of fine crystals or powder, wherein said fine crystal- or powder-form isocyanate composition is prepared by
(1) reacting an organic isocyanate with 2-methyl-1,3-propanediol in quantities such that from 1.2 to 6 moles of said organic isocyanate are used for each mole of 2-methyl-1,3-propanediol, and
(2) grinding or milling the product formed in (a)(1), with
(b) an isocyanate-reactive compound.

* * * * *